US008294716B2

(12) United States Patent
Lord et al.

(10) Patent No.: US 8,294,716 B2
(45) Date of Patent: Oct. 23, 2012

(54) DISPLAY OF TRENDS AND ANTICIPATED TRENDS FROM MITIGATION

(75) Inventors: William P. Lord, Fishkill, NY (US); Xinxin (Katie) Zhu, Croton-on-Hudson, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 855 days.

(21) Appl. No.: 12/302,359

(22) PCT Filed: May 1, 2007

(86) PCT No.: PCT/US2007/067851
§ 371 (c)(1),
(2), (4) Date: Nov. 25, 2008

(87) PCT Pub. No.: WO2007/143300
PCT Pub. Date: Dec. 13, 2007

(65) Prior Publication Data
US 2009/0231341 A1 Sep. 17, 2009

Related U.S. Application Data

(60) Provisional application No. 60/803,512, filed on May 31, 2006.

(51) Int. Cl.
*G06T 11/20* (2006.01)
(52) U.S. Cl. ...................................................... 345/440
(58) Field of Classification Search .................. 345/440, 345/440.1
See application file for complete search history.

(56) References Cited

U.S. PATENT DOCUMENTS

| | | | | |
|---|---|---|---|---|
| 6,251,081 | B1 * | 6/2001 | Narimatsu | 600/490 |
| 2004/0267142 | A1 | 12/2004 | Paul | |
| 2004/0267321 | A1 | 12/2004 | Boileau et al. | |
| 2005/0119534 | A1 * | 6/2005 | Trost et al. | 600/300 |
| 2005/0246366 | A1 * | 11/2005 | Kouchi et al. | 707/102 |
| 2006/0289342 | A1 | 12/2006 | Sugioka et al. | |
| 2007/0088525 | A1 * | 4/2007 | Fotiades et al. | 702/131 |
| 2007/0198301 | A1 * | 8/2007 | Ayers et al. | 705/3 |
| 2008/0319331 | A1 * | 12/2008 | Zizzo et al. | 600/511 |

FOREIGN PATENT DOCUMENTS

| | | |
|---|---|---|
| WO | 2004074966 A2 | 9/2004 |
| WO | 2005057175 A2 | 6/2005 |
| WO | 2005096920 A1 | 10/2005 |

OTHER PUBLICATIONS

Bansal, et al., "A Computer-Based Intervention on the Appropriate Use of Arterial Blood Gas" http://adams.mgh.harvard.edu/PDF_Repository/D010001574.pdf on Dec. 21, 2005. Y Huang et al., "Evaluation of Outcome Prediction for a Clinical Diabetes Database", Proc. Int. Symposium KELSI 2004, pp. 181-190 (2004).

Takekawa, A. et al., "A Mathematical Model for the Clinical States of Acute Leukaemia and the Estimation of Clinical Quantities, Using the Model", Trans. Institute of Electronics and Communication Engineers of Japan, Part A, vol. J67A, No. 3, pp. 220-227, Mar. 1984.

* cited by examiner

*Primary Examiner* — Ryan R Yang

(57) ABSTRACT

An electronic display (10") includes a graph representing a magnitude of a sensed physiological condition versus time. A background behind the graph is color coded delineated, such as to depict a normal range for the physiological condition and one or more abnormal ranges. This provides instant color-coded feedback to the clinician of the meaning of the graph. When a clinician selects a medication or treatment, a database is searched to generate an expectation range (42a, 42b, 42c, 42d, 44a, 46c) depicting how the sensed physiological condition is expected to move after administration of the medication or treatment. This enables the clinician to compare treatments and, after a treatment is selected, to receive easy-to-interpret feedback as to whether the sensed physiological condition is responding as expected to the treatment.

25 Claims, 3 Drawing Sheets

DISPLAY OF TRENDS AND ANTICIPATED TRENDS FROM MITIGATION

CROSS REFERENCE TO RELATED APPLICATIONS

This application claims the benefit of U.S. provisional application Ser. No. 60/803,512 filed May 31, 2006, which is incorporated herein by reference.

The present application is directed to making the significance of displays, particularly diagnostic displays, more immediately meaningful to the viewer. It finds particular application in conjunction with medical displays, particularly medical displays of trends and anticipated trends and will be described with particular reference thereto. However, it is to be appreciated, that the present application will also be applicable to other types of displays.

Patients, particularly patients in a hospital or other care facility, are commonly monitored by one or a plurality of monitors. The sensor unit which senses a physiological condition, such as blood pressure, temperature, blood oxygen, and the like is typically connected with a display unit. Commonly, the display unit is a printer which prints an elongated paper strip or chart which displays a plot or graph of the monitored physiological condition versus time. When plural physiological conditions are monitored, individual charts can be generated for each condition or two or more of the conditions can be displayed superimposed or offset on the same paper chart, typically with a different color ink. To facilitate interpretation, the paper chart is pre-printed with a scale or scales if designed for multiple physiological conditions.

Although paper charts are still commonly used, many have been replaced by electronic charts which emulate the paper chart on a video display. A graph of the monitored physiological condition versus time is displayed on a monitor superimposed on a background scale which relates the graph of the physiological condition versus time to a scale with the normal range for that physiological parameter, such as a temperature scale from 95°-105° F. for a temperature sensor. The most recently monitored data is displayed, while older data is stored in memory for later recall, if necessary. Again, multiple physiological conditions can be monitored and displayed on the same display, such as with graphs or curves of different colors.

These displays, although accurate and correct, require interpretation. The examining doctors, nurses, respiratory therapists, patients and/or patients' families in for home monitoring, paramedics and/or EMTs on ambulances, etc., hereinafter clinician, must determine whether the value of the monitored physiological condition is normal, high, or low and, if high or low, whether the value is acceptable or in a danger zone. This can be time-consuming and is subject to human error.

To assist in recognizing and providing a warning if the value of a physiological condition reaches a danger zone, many monitors have an audio or visual alarm, such as a buzzer or flashing light. If the graph of the measured physiological condition enters a danger zone, the alarm is sounded.

While effective, the conditions for which some patients are hospitalized cause one or more of their monitored physiological conditions to be in a danger zone. The monitored physiological condition may remain in the danger zone for some time while medical treatments are applied to correct the problem. To have the alarm sound or flash continuously during this extended time conveys little meaningful information to the clinician. Indeed, because the alarms can be annoying, they are often turned OFF, thereby providing no additional information to the clinician.

Further, the current displays provide a graphical display of the current and past values of the monitored physiological conditions. Projections of future trends are absent. That is, as the medical treatment is being provided to bring the monitored physiological condition out of the danger zone, there is no display of the expected trend or reaction to the treatment. A clinician must analyze the chart and make a mental determination regarding whether the patient is reacting as anticipated or whether the medical treatment should be modified.

The present application provides a new and improved display technique which overcomes the above-referenced problems and others.

In accordance with one aspect, an electronic display is provided. A graph displays a physiological condition value or amplitude versus time. A background for the graph includes at least one range which is delineated, e.g., color-coded, to indicate a normal range for the sensed physiological condition and at least a second range which is delineated to indicate an abnormal value of the monitored physiological condition.

In accordance with another aspect, a method of generating this display is provided. A physiological condition to be monitored is determined, a current value of it is sensed, and the graph is plotted. The normal and abnormal ranges for the physical condition are determined and the background is generated with the normal physiological condition range in a first characteristic delineation and the abnormal range in a second characteristic delineation. The graph is superimposed on the background.

In accordance with another aspect, a method of generating the display is provided. A current value of a physiological condition is sensed and a graph representing a magnitude of the sensed physiological condition versus time is generated on the electronic display. A medication or medical treatment to be administered to the patient is selected. An expectation range which illustrates a range within which the sensed physiological condition is expected to move after the administration of the selected medication or treatment is generated and displayed on the electronic display.

In accordance with another aspect, an apparatus for displaying sensed physiological conditions is provided. The apparatus includes a means for sensing a current value of a physiological condition, an electronic display, and a means for generating a graph representing the magnitude of the sensed physiological condition on the electronic display. A means is provided for inputting a selected medication or treatment for administration to the patient. A means generates an expectation range which is displayed on the electronic display to illustrate a range within which the sensed physiological condition is expected to move after administration of the input medication or treatment.

One advantage resides in a display of data in such a way that both trends and expectations are clear.

Another advantage is in the generation of dynamically varying norms or expected values over time.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
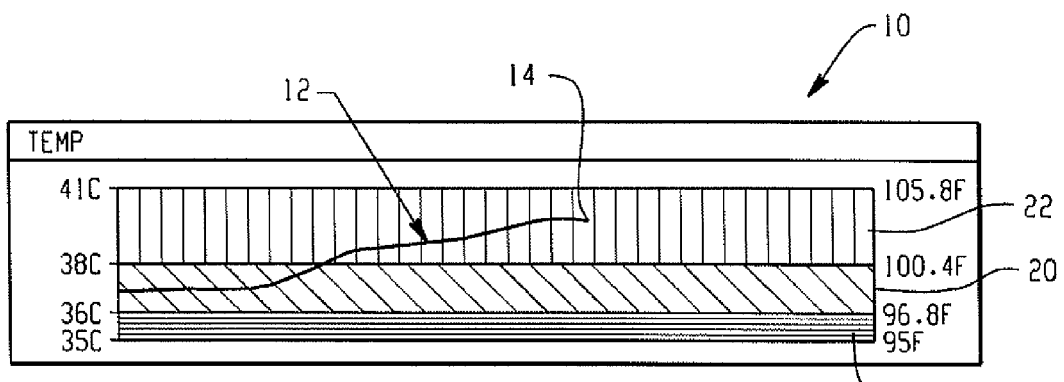
FIG. 1 is a graphic display of an exemplary patient's temperature over time as compared to expected ranges.

With reference to FIG. 1, a display 10, temperature in the illustrated embodiment of FIG. 1, includes a graph 12 displayed on a vertical axis representative of temperature and a horizontal axis representative of time. An end position 14 of the graph is indicative of the current time. The time scale can be predefined or selectable to view the graph over a longer or shortened time period. The graph 12 is superimposed on a background in which a normal temperature range 20 is delineated in a first manner, e.g., color-coded green, an abnormally high temperature range 22 is delineated in a second manner, e.g., color-coded in red, and an abnormally low temperature range 24 is delineated in a third manner, e.g., color-coded in blue. Other delineated selections may, of course, be selected as may be appropriate to connote the normal and abnormal ranges. Although the delineations are described in terms of color, other delineations, such as cross-hatching, labeling, patterning, and the like are also contemplated. The other delineations can also be used in conjunction with color-coding to assist color-blind clinicians.

Figure 2:
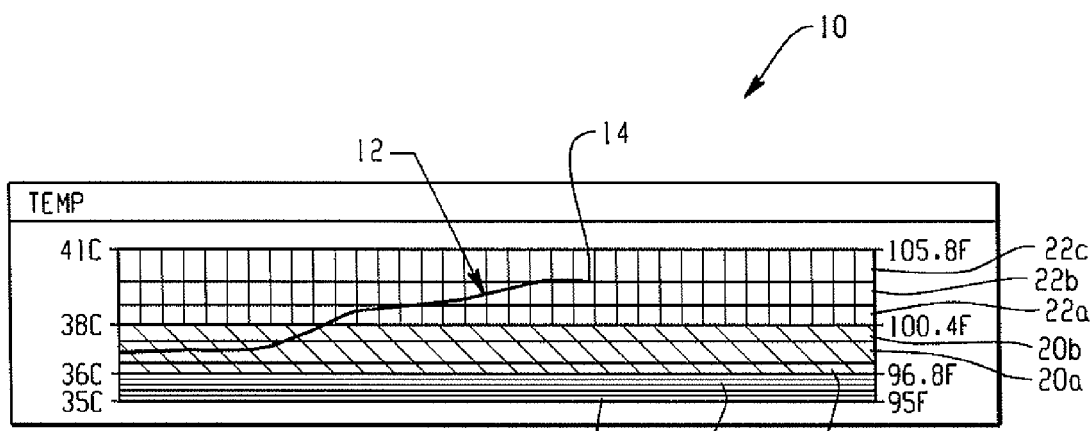
FIG. 2 is a graph showing degrees of severity within each of the expected ranges.

Instead of denoting merely normally, high, and low ranges, further gradations can be provided. For example, an interface between normal and abnormal might be color-coded in yellow to denote warning, but possibly not danger. With reference to FIG. 2, finer grain ranges for the normal and abnormal values can be produced. In FIG. 2, the high range has been broken down into three sub-ranges 22*a*, 22*b*, 22*c* which are color-coded in progressively more intense shades of red for subranges from slightly high to very high. Similarly a slightly low range 24*a* and a very low range 24*b* are also color-coded in a lighter shade and a more intense shade of blue. The acceptable range is also segmented into sub-ranges with lighter and darker shades of green 20*a*, 20*b*. Preferably, finer grain ranges are selected such that each has associated with it actions to be carried out when a patient's actual physiological condition value being measured enters that range. The interfaces between the finer grain ranges are selected to correspond with temperatures, in the illustrated, which trigger such medical action. These ranges can also represent standard deviations in specific populations, medical opinion, and the like.

Although FIGS. 1 and 2 show graphs of temperature, by way of example, it is to be appreciated that the information shown on the graph is typically based on the condition on which the patient is being evaluated, such as mean arterial pressure, heart rate, respiratory rate, blood oxygen, or the like. For different physiological conditions, the units for both of the value or the magnitude of the condition and time will typically change as will the normal and abnormal ranges. Moreover, the various ranges can be labeled with superimposed text or other indications that are readily recognized, particularly by observers who suffer from color blindness.

Figure 3:
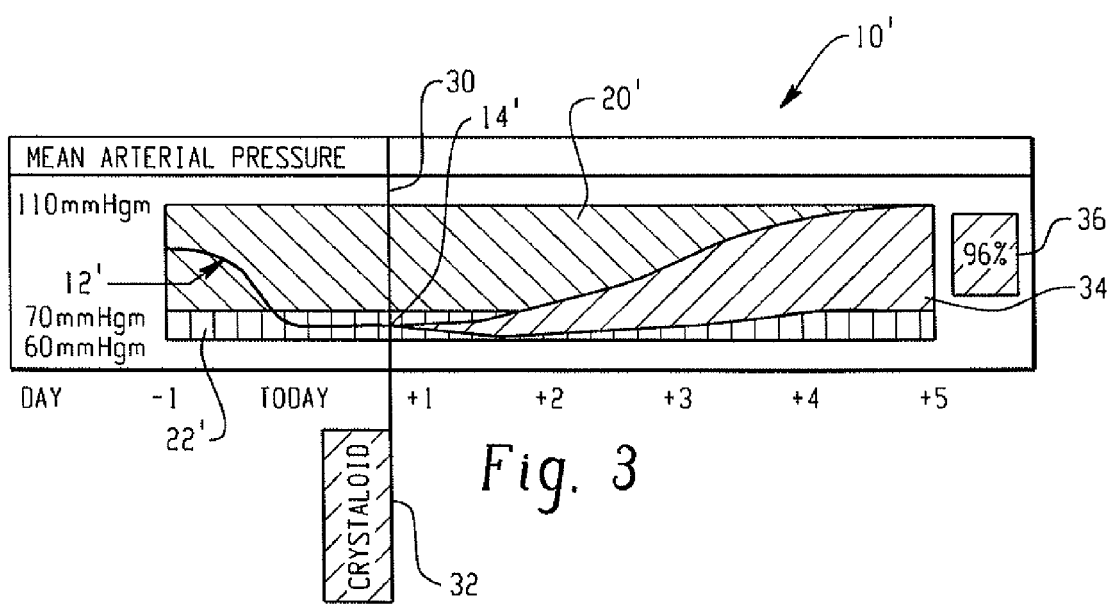
FIG. 3 is a graph showing expected blood pressure response to medication.

Unlike FIGS. 1 and 2 in which the previously described displayed ranges of data categories are set by static functions, i.e., ranges staying the same over time, the ranges may also be dynamic to show an expected response. With reference to FIG. 3, a display 10' depicts a graph 12' depicting mean arterial pressure, by way of example. The display is color-coded to denote a normal region 20' and an abnormal region 22'. An end 14' of the graph indicates the current time, or 'now'. In this exemplary FIGURE, the plot of the patient's actual mean arterial pressure has dropped too low, calling for a medical response. In the present example, the medical response is to give the patient crystalloid at the current time. A graphic marker or indicator 30 indicates the time at which a medical treatment is administered and a label 32 indicates the nature of the medical treatment. As described in greater detail below, the clinician inputs the medical treatment administered. Given the patient's current physiological condition level and the nature of the treatment, a graphical indication 34 of the expected range of the monitored physiological condition is displayed superimposed on the normal and abnormal range displays. The values for the ranges can be generated by data mining of patients with similar conditions and backgrounds that have had a known positive outcome with the selected medication or treatment in question, a database loaded in accordance with the opinions of expert panels, the expectations of the prescribing clinician, chemical or physiological research and analysis, or the like. The expected displayed range 34 and the stall-up treatment marker 30 are like color-coded to facilitate easy understanding of displays in which multiple medications are administered at different times.

In a "inquiry mode" method of use, the diagnosing clinician selects each of a plurality of potential treatments or medications and reviews the generated expectation display range. In this manner, the diagnosing clinician can try several potential treatments or medications and use the generated display to help select the most appropriate. As an enhancement, a probability of success indication 36 is also added to the display. That is, when the expectation range 34 is based on successful applications of the designated treatment, the probability of success number is based on the proportion of patients, in like conditions, who were successfully treated with this medication or treatment. In the illustrated embodiment, the probability of success is represented by a graphical depiction of the percentage of patients successfully treated. Of course, other indications could also be used, such as a green-yellow-red color coding to show very high, marginal, and poor probabilities of success compared to other potential treatments. Probabilities of success can also be provided for each expectation range or portions of each expectation range. For example, the expectation range can be subdivided into subranges, such as subranges indicative of a 50%, 75%, and 95% likelihood of success. Various other probability of success indicators are also contemplated.

Figure 4:
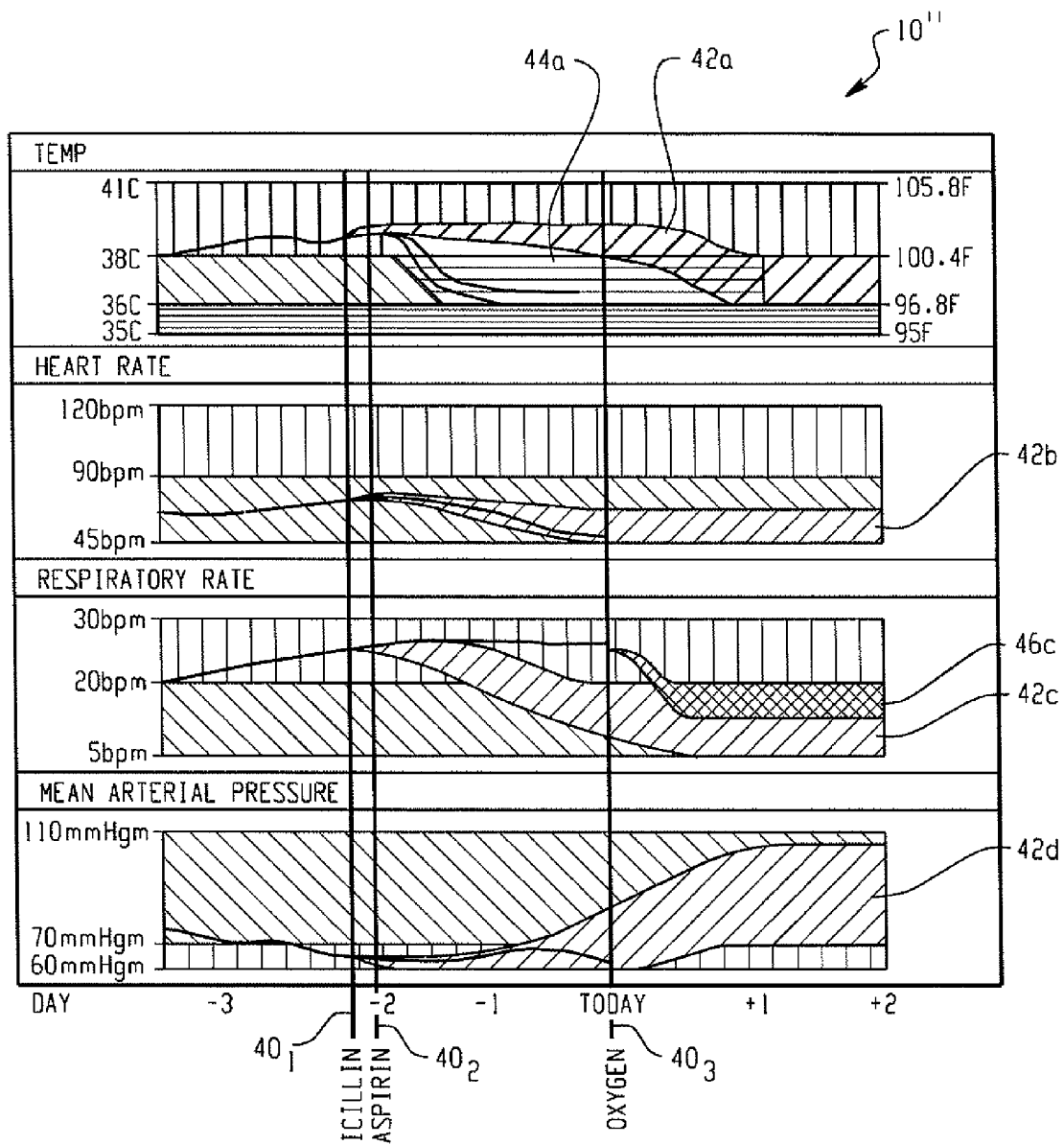
FIG. 4 is a graph showing multiple monitored parameters and their responses to selected treatments or medications.

With reference to FIG. 4, frequently a plurality of parameters will be monitored concurrently and a plurality of treatments or medications will be applied to the monitored patient. In the present example, four conditions are monitored—temperature, heart rate, respiratory rate, and mean arterial pressure. It will be seen in display 10" that about four days ago, the patient's temperature moved up into the abnormally high range as did the patient's respiratory rate. By about three days ago, the patient's temperature was recovering slightly, but the respiratory rate was still increasing and the mean arterial pressure was approaching the abnormally low range. About 2⅓ days ago, the patient's temperature started rising again, the respiratory rate continued to climb in the abnormally high range, and the mean arterial pressure trended downward deeper into the abnormally low range. As indicated by marker 401, a first treatment was administered, amoxicillin in the present example. When the amoxicillin as administered, correspondingly color-coded expectation range displays 42*a*, 42*b*, 42*c*, 42*d* were generated and overlaid on the displays.

Soon thereafter, a second treatment denoted by marker 402, aspirin in the illustrated example, was administered. Because aspirin is only expected to have an effect on temperature and not the other monitored conditions, a second treatment expectation range 44a was overlaid on the temperature chart.

About a day ago, the temperature and heart rate were both nicely in the normal range and the mean arterial blood pressure was approaching the normal range. Respiration rate was still abnormally high. At the present time, the temperature and heart rate appear in the normal range but the respiration rate still remains abnormally high and was not decreasing according to the expectation display 42c. The mean arterial blood pressure is still in the abnormally low range, but within the expected range 42d. To bring the patient's vital signs back towards normal, the decision is made to start a third treatment, in the present example, administer oxygen, which is denoted by a third treatment marker $40_3$. A third treatment expectation curve 46c is added to the graphs. Specifically, since oxygen is only expected to improve the respiratory rate, the third treatment expectation curve 46c is generated and superimposed on the respiratory rate display. Looking out one day, it is seen that by that time, the amoxicillin, which is a slower temperature reducer than is aspirin because it addresses to the underlying cause of the elevated temperature rather than the symptom, is expected to have brought the temperature into the normal range. Hence, the symptom-only treatment of aspirin is scheduled to be terminated. With these three treatments, the expected ranges are predicting that all four illustrated vital signs will be in the normal range by tomorrow. Of course, if the graphs 12 fail to remain within the expected ranges 42a, 42b, 42c, 42d, 46c, additional or different future treatments/medications can be expected to be administered. Optionally, the attending clinician can turn OFF the expectation range for any one or more of the treatments. By toggling the expectation ranges ON and OFF, the clinician can check whether each treatment is working as expected.

In the example of FIG. 4, aspirin and amoxicillin are complementary drugs in that aspirin addresses the symptoms rapidly while amoxicillin addresses the underlying cause more slowly. In other instances, interacting drugs or treatments may be administered in which the two together act synergistically to achieve a different expectation that either one individually or the sum of the two. For interacting drugs, the pair or more of interacting drugs can be treated as a single treatment or medication denoted by a single expectation range display.

Figure 5:
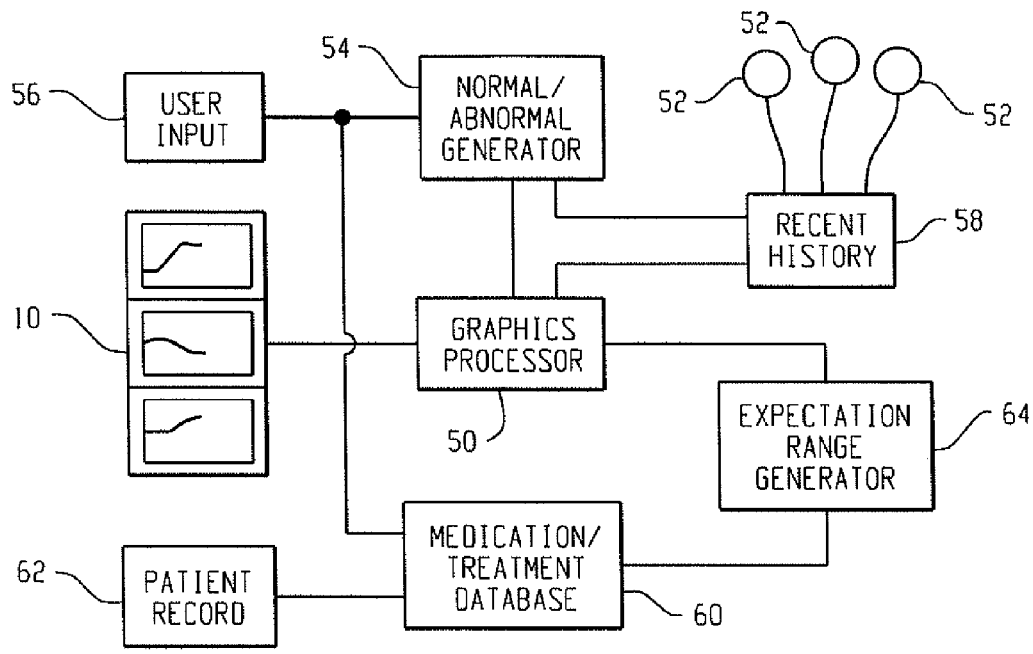
FIG. 5 is a diagrammatic illustration of a system for generating the displays of FIGS. 1-4.

With reference to FIG. 5, the display unit 10, 10', 10", (hereinafter 10) associated with each patient includes a graphics controller 50 which converts signals from one or more physiological condition sensors 52 and other electronic information into the displays discussed above. In one embodiment, each of the sensors identifies itself to a range display generator or algorithm 54 which recognizes whether the sensor is a temperature sensor, heart rate sensor, etc. and causes the graphics processor 50 to generate the corresponding normal and abnormal ranges, as well as the appropriate units, e.g., degrees C. or F, beats per minute, etc. Alternately, an operator input device 56 can be used to identify the sensors and select or modify the normal and abnormal condition ranges. A recent history memory 58 stores the sensed condition values for at least the duration of the graph 12 shown on the display 10 and preferably longer. The display may be adjacent the patient, at a nurses' station, at a clinician's remote office, or the like. For example, the display can be communicated over the Internet to a display terminal at a remote hospital(s) where a team of experts can be consulted. Multiple displays, connected by wire, wirelessly, etc. are also contemplated. Further, alarms may be provided at the monitor or at a remote location(s) using wired or wireless protocols. The alarm information can be sent over the data channel to a remote monitor location.

To generate the expectation ranges discussed in conjunction with FIGS. 3 and 4, an operator uses the input device 56 to input proposed or actually administered medications or treatments into a database 60, which database is pre-programmed with corresponding expectation ranges 34, 42a, . . . , 46c for each of a plurality of medications and treatments based on the opinions of expert panels. Preferably, the database 60 is pre-programmed with a plurality of expectation ranges for each medication or treatment corresponding to different current patient conditions. The database can be a preprogrammed memory in the bedside device, a remote database, such as one in the clinic's intranet. Multiple databases which might be remotely accessed, such as a database maintained by the manufacturer of each treatment, by a medical journal, by trade groups, by medical schools, etc. are also contemplated. In order to select among the plurality of expectation ranges for each medication or treatment, the database also receives the recent patient condition values from the memory 58 and other patient background information from a patient information or record file 62. An expectation range display generator 64 converts the information from the database 60 into appropriate instructions for the graphics processor 50. Optionally, the current physiological condition readings from the sensor are conveyed to the range generator in order to match the starting point of the expectation range with the current condition values. For example, if the database only has a fixed plurality of discrete expectation ranges, the expectation range generator 64 may interpolate between the two closest expectation ranges to move the origin into alignment with the current values.

Figure 6:
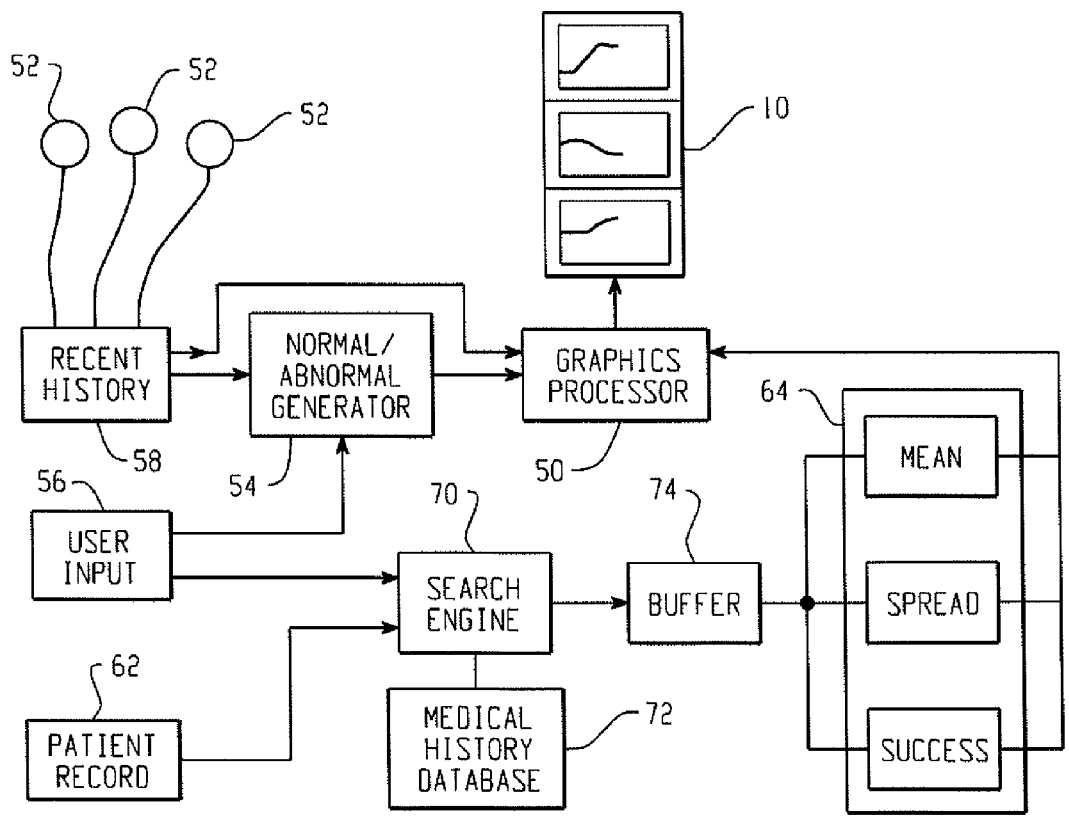
FIG. 6 illustrates an alternate system of generating the displays of FIGS. 1-4.

With reference to FIG. 6, the potential drug or treatment from the input device 56, and the patient condition information from the memory 58, and the patient information database 62 are input into a search engine 70. The search engine searches a medical history database 72 for patients with similar medical histories to whom the input medication or treatment was administered. In one embodiment, the database 72 is the database of the hospital at which the treatment is given. In another embodiment, the database is a larger database, such as a database of all patients of the network with which the hospital is associated. The database can also be a national database, such as a database which specializes is specific types of illnesses, databases at the Center for Disease Control, or the like. The charts from patients with similar medical conditions treated with the same medicine or treatment are collected in a memory or buffer 74. The expectation range generator 64 includes an algorithm or routine 76 for determining the mean or median versus time response of the successfully treated patients from the buffer 74. An algorithm or routine 78 determines the spread or range versus time of the various physiological conditions of the successfully treated patients from the buffer 74. A probability of success routine or algorithm 80 analyzes the patient data in the buffer 74 to determine a probability that the treatment will be successful, e.g., the percentage of patients with whom the treatment was successful. When multiple physiological conditions are displayed, the mean or median versus time and the range versus time calculations are performed for each displayed physiological condition or at least those physiological conditions which the medication or treatment was intended to address. The information is conveyed to the graphics processor 50 which converts the expectation range data into the appropriate expectation range display on the displays 10. The graphics processor also receives the normal/abnormal background range displays from the normal/abnormal range generator 54, the current sensed physiological condition values from the sensors 52, and prior sensed condition values from the memory 58.

In addition to devices assigned and built to perform these functions, older monitors can be upgraded by software reprogramming, plug-in upgrades, interfacing with an add-on or remote device to add functionality, or the like.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. An electronic display unit configured to generate an electronic display comprising:
    a graph displaying physiological condition values versus time;
    a background for the graph including at least one range which is delineated to indicate a normal range for the physiological condition values and at least a second range which is delineated to indicate an abnormal range of the physiological condition values;
    an expectation range indicating an expected range of the physiological condition versus time in response to an administered medication or treatment, the expectation range being superimposed on the background; and
    a marker indicative of when a medication or treatment was administered and a display of the nature of the medication.

2. The electronic display unit according to claim 1, the generated electronic display further including:
    a plurality of temporally aligned medical treatment displays, each of the medication/treatment indicating markers indicative of the time when a medical treatment was administered being a line superimposed on the plurality of displays; and
    wherein the expectation range extends from each medication/treatment indicating display forward in time, the sensed medical condition graph being superimposed on at least some of the displayed expectation range.

3. The electronic display unit according to claim 2, wherein each of the medication/treatment indicating displays and the corresponding expectation range have corresponding delineated sections.

4. The electronic display unit according to claim 1, wherein the normal and abnormal ranges are delineated by color-coding.

5. A method performed by the electronic display unit of claim 1, comprising:
    determining a physiological condition to be monitored;
    sensing a current value of the physiological condition;
    plotting the graph of the sensed physiological condition versus time;
    determining the normal and abnormal ranges for the determined physiological condition;
    generating a background for the normal physiological condition range in a first characteristic delineation and for the abnormal range in a second characteristic delineation;
    superimposing the graph, the marker, and the nature of the medication on the background.

6. The electronic display unit of claim 1, comprising:
    means for sensing a current value of the physiological condition;
    means for plotting the graph from the monitored physiological condition versus time;
    means for determining the normal and abnormal ranges for the monitored physiological condition;
    means for displaying the background with the normal physiological condition range in a first characteristic delineation and the abnormal range in a second characteristic delineation.

7. The electronic display unit of claim 1, comprising:
    means for sensing a current value of the physiological condition;
    means for generating a graph on the electronic display representing magnitude of the sensed physiological condition versus time;
    means for inputting a medication or medical treatment for administration to the patient;
    means for generating an expectation range display on the electronic display illustrating a range within which the sensed physiological condition is expected to move after administration of the input medication or treatment.

8. A method for generating a display comprising:
    receiving a current value of a physiological condition of a patient sensed by a patient sensor;
    generating a graph on an electronic display device, the generated graph representing a magnitude of the sensed physiological condition versus time;
    generating an expectation range for each of one or more medications or medical treatments to be administered to the patient and displaying one or more of the expectation ranges corresponding to one or more selected medications or medical treatments on the electronic display device in conjunction with the graph, each expectation range illustrating a range within which the sensed physiological condition is expected to move after administration of the selected one or more medications or medical treatments.

9. The method according to claim 8, further including:
    generating a background for the graph and the one or more displayed expectation ranges, the background delineating a normal range for the sensed physiological condition and an abnormal range of the sensed physiological condition.

10. The method according to claim 8, further including:
    using the one or more displayed expectation ranges to set a course of treatment.

11. The method according to claim 8, wherein the selected treatment includes a plurality of complementary medications that act independently to address a common condition.

12. The method according to claim 8, further including a plurality of expectation displays.

13. The method according to claim 12, further including:
    generating visual markers of each medication or treatment and a time of commencing administration.

14. A non-transitory computer readable medium carrying software which controls one or more processors to perform the method according to claim 8.

15. An apparatus for displaying sensed physiological conditions, including:
    a database which stores medical information regarding expected responses to each of a plurality of medications and medical treatments;
    an operator input device by which an operator inputs into the database a selected medication or medical procedure to retrieve corresponding expectation data;

an electronic monitor;

an expectation range display generator which converts the data from the database into instructions for an expected range display which illustrates a range within which the sensed physiological condition is expected to move after administration of the input medication or treatment;

a graphics processor which converts the instructions from the expectation range display generator into appropriate control signals for the electronic monitor to display a graph representing a sensed physiological condition versus time in conjunction with expected range of the selected medication or medical procedure.

16. The apparatus according to claim 15, further including:
a patient information electronic record, the database being connected with the patient information electronic record to receive patient information and with a patient sensor which senses values of the sensed physiological condition.

17. The apparatus according to claim 15, the database stores actual patient responses to each of a plurality of medications or medical treatments and further including:
a search engine which receives the selected medication or medical treatment to be administered to the patient and searches the database and retrieves graphs of patients to whom medication or medical treatment had been administered.

18. The apparatus according to claim 17, wherein the expectation range display generator includes:
a routine or algorithm for determining a mean or median of the sensed physiological condition versus time from the retrieved patient graphs;
a routine or algorithm for calculating a range or deviation versus time of the sensed condition from the retrieved graphs.

19. The apparatus according to claim 17, wherein the expectation range display further includes:
a routine or algorithm which determines at least one probability of success from the retrieved patient graphs.

20. The apparatus according to claim 15, further including:
a graphics processor for controlling the electronics display, the graphics processor being adapted to be connected with at least one sensor for sensing the physiological condition and converting the sensed physiological condition into the graph of the physiological condition amplitude versus time;
a normal/abnormal range generator for generating instructions to the graphics processor concerning a normal range of the sensed physiological condition and at least one abnormal range, the graphics processor color-coding a background to the graph indicating the normal range in a first color and the abnormal range in a second color.

21. The apparatus according to claim 15, wherein the graphics processor superimposes the graph on the expectation range such that the operator can see how well the sensed physiological condition correlates to the expectation range after the selected medication or treatment is administered.

22. A method of generating a display comprising:
generating a background including at least one range delineated to indicate a normal range for a physiological condition and an abnormal range for the physiological condition;
sensing the physiological condition;
on a user input, selecting each of a plurality of candidate medications or treatments to be administered;
generating a corresponding expectation range superimposed on the background for each candidate medication or treatment illustrating a range in which the sensed physiological condition is expected to move after administration of the selected one or more medications or treatments;
displaying a graph superimposed on the background representing magnitude of the sensed physiological condition versus time and a depiction of the expectation ranges corresponding to the selected candidate medications or treatments on a display device; and
selecting one or more of the candidate medications or treatments based on the generated expectation ranges.

23. The method according to claim 22, further including:
upgrading an existing patient monitor to perform the method of claim 22.

24. The method according to claim 22, further including:
sensing the physiological condition at one location;
generating the graph and expectation range at a remote location to facilitate remote viewing.

25. An apparatus for displaying sensed physiological conditions, comprising:
an electronic display device; and
one or more processors configured to:
receive sensed values of a physiological conditions from a patient sensor,
generate a graph based on the sensed values depicting changes in the sensed physiological condition with time,
generate a background for the graph including at least one range which is delineated to indicate a normal range for the physiological condition and at least a second range which is delineated to indicate an abnormal range for the physiological condition;
receive an input indicating when a medication or treatment is administered,
generate an expectation range indicating an expected range of the physiological condition versus time in response to administration of the medication or treatment, and
control the electronic display device to display the graph, the background and the expectation range superimposed on the background, a marker indicating when the medication or treatment was administered, and a display of the nature of the medication or treatment.

* * * * *